United States Patent [19]

Hutchings et al.

[11] 4,288,372

[45] Sep. 8, 1981

[54] PRODUCTION OF MALEIC ANHYDRIDE

[75] Inventors: Graham J. Hutchings; Raymond Higgins, both of Middlesbrough, England

[73] Assignee: Imperial Chemical Industries Limited, London, England

[21] Appl. No.: 100,141

[22] Filed: Dec. 4, 1979

Related U.S. Application Data

[62] Division of Ser. No. 906,251, May 15, 1978, Pat. No. 4,209,423.

[30] Foreign Application Priority Data

May 23, 1977 [GB] United Kingdom ............... 21610/77
Jan. 30, 1978 [GB] United Kingdom ................. 3686/78

[51] Int. Cl.³ ........................................... C07D 307/60
[52] U.S. Cl. ............................. 260/346.75; 260/346.4
[58] Field of Search .................................... 260/346.75

[56] References Cited

U.S. PATENT DOCUMENTS

| | | | |
|---|---|---|---|
| 3,156,705 | 11/1964 | Kerr | 260/346.75 |
| 3,864,280 | 2/1975 | Schneider | 252/435 |
| 3,888,886 | 6/1975 | Young et al. | 260/346.75 |
| 3,915,892 | 10/1975 | Harrison | 252/435 |
| 3,985,775 | 10/1976 | Harrison | 260/346.75 |
| 3,987,063 | 10/1976 | Lemal et al. | 260/346.75 |
| 4,016,105 | 4/1977 | Kerr | 252/437 |
| 4,017,521 | 4/1977 | Schneider | 260/346.75 |
| 4,049,574 | 9/1977 | Kerr | 252/435 |
| 4,071,539 | 1/1978 | Kerr et al. | 260/346.75 |
| 4,105,586 | 8/1978 | Kerr | 252/435 |
| 4,123,388 | 10/1978 | Kerr et al. | 252/437 |
| 4,152,338 | 5/1979 | Kerr | 260/346.75 |
| 4,153,577 | 5/1979 | Barone | 252/435 |
| 4,158,671 | 6/1979 | Barone | 252/435 |

FOREIGN PATENT DOCUMENTS 1416099 12/1975 United Kingdom .
1464198 2/1977 United Kingdom .

Primary Examiner—Henry R. Jiles
Assistant Examiner—Bernard Dentz
Attorney, Agent, or Firm—Cushman, Darby & Cushman

[57] ABSTRACT

Catalysts for the oxidation of hydrocarbons to acid anhydrides, for example maleic and phthalic anhydrides, are prepared from a vanadium/phosphorus mixed oxide precursor by conditioning it by contact with a strong acid of concentration at least 3N and solvent extraction to remove unwanted phases. The treated precursor is converted to a catalytically active form by heating. Novel catalysts containing phase X are produced. The catalysts may contain rare earth metal promoters.

1 Claim, No Drawings

PRODUCTION OF MALEIC ANHYDRIDE

This is a division of application Ser. No. 906,251 filed May 15, 1978 now U.S. Pat. No. 4,209,423.

This invention relates to the production of acid anhydrides especially maleic anhydride and catalysts therefor.

It is known to produce maleic anhydride by oxidising hydrocarbons, for example benzene or hydrocarbons having the formula R'—CH$_2$—CH$_2$—CH$_2$—CH$_2$R" where R' and R" are individually hydrogen or alkyl groups, R' and R" having together at most six and preferably at most four carbon atoms, or cyclo-alkanes having a —CH—CH$_2$—CH$_2$—CH— group, preferably in a ring, for example cyclohexane. Mixtures of hydrocarbons, for example naphtha, may be used but n-butane is a preferred feedstock. n-Butenes may be used. The hydrocarbon is generally oxidised by contacting it in the vapour phase together with oxygen with a solid catalyst and recovering maleic anhydride from the product. Oxygen may be provided in the form of air by mixing the hydrocarbon in a concentration generally, except in the case of fluidised bed processes, lower than the lower explosive limit with air and contacting the mixture with the catalyst under appropriate conditions of temperature and pressure (the "fuel lean" system). In this case the product gas, after recovery of maleic anhydride, is usually vented or burned. The oxidation may also be carried out as disclosed in German Offenlegunschrift No. 2,412,913 by mixing the hydrocarbon with air in a concentration higher than the upper explosive limit, contacting it with a catalyst under appropriate conditions of temperature and pressure and recovering maleic anhydride from the product gas (i.e. a "fuel rich" system). It is possible to operate within the explosive limits using a fluidised bed reactor.

It is important that the catalyst should have a high selectivity, that is that the yield of maleic anhydride should be as high as possible based on the hydrocarbon consumed in the process. In processes in which the product gas after recovery of maleic anhydride is vented or burned it is important, therefore, that the pass yield should be high, i.e. that the proportion of the hydrocarbon converted to maleic anhydride on a single pass should be as high as possible. If any unconverted hydrocarbon is recycled it is desirable that a high pass yield should be achieved in order to avoid recycling an unduly high proportion of the hydrocarbon but the selectivity in terms of the yield of maleic anhydride based on the hydrocarbon consumed in each pass is relatively more important.

It is an object of this invention to provide catalysts for the oxidation of hydrocarbons to maleic anhydride which possess an acceptable selectivity as judged in the case of a "fuel lean" system by the pass yields obtainable with them under suitable conditions and in the case of a "fuel rich" system by the selectivities based on the hydrocarbon consumed at an acceptable conversion under suitable conditions.

Catalysts for the oxidation of hydrocarbons to maleic anhydride have been made by reacting a vanadium compound with phosphoric acid in an acid solution, evaporating to dryness to give a vanadium/phosphorus mixed oxide catalyst precursor and activating the catalyst by heat treatment. The solution may be an aqueous solution as disclosed for example in British Pat. No. 1,409,094 or a solution in an organic solvent for example as described in British Pat. No. 1,416,099.

The catalyst precursor may alternatively be precipitated by the addition of water to the vanadium/phosphoric acid solution under controlled conditions for example as described in South African patent application No. 41 of 1976. The latter technique however is difficult to control and requires an extra filtration stage as compared with a process for producing the precursor which merely involves evaporating the precursor solution. Evaporation of the precursor solution however tends to produce a mixture of compounds and phases and on activation the catalyst tends to have a low surface area. We have found that one material which is present and is deleterious is that identified by G. Ladwig in Z. Chem. 1968 Vol. 8, pages 307 & 308 as a hydrogen phosphate without strong H-bonding of formula VO(H$_2$PO$_4$)$_2$, which is herein referred to as phase E.

This invention provides a process for producing a catalyst for the production of acid anhydrides especially maleic anhydride which comprises reacting a vanadium compound with phosphoric acid, producing a solid vanadium/phosphorus mixed oxide catalyst precursor, contacting the solid precursor with an acid stronger than H$_3$PO$_4$ (judged in terms of its first dissociation constant in water), which is preferably non-oxidising, at a concentration of at least 3 N and preferably at least 5 N, preferably in an aqueous solution, recovering the precursor and extracting it with water or with another solvent for phase E for example dimethyl sulphoxide until substantially only material insoluble in water or the said solvent is left, separating the precursor and producing a phase transition to a catalytically active form by heating it.

The precursor may dissolve in the strong acid and be recovered from it by distilling the strong acid from it.

The phase transition occurs at the temperatures normally encountered in the production of the acid anhydrides, and thus it may not be necessary to carry it out before use. If desired the phase transition may be carried out before use by heating to a temperature of for example 340° to 500° C.

The process may suitably be carried out by reacting the vanadium compound with phosphoric acid in an acidic solution which is suitably an aqueous acidic solution and precipitating a vanadium/phosphorus mixed oxide catalyst precursor by removing solvent, preferably at least 90% and more preferably at least 95% of the solvent being removed, preferably leaving a dry or nearly dry solid.

The catalytically active form of the catalyst normally comprises the beta form (phase B). The characteristics of the beta form are disclosed in U.S. Pat. No. 3,864,280. The beta form is readily produced from the B' form which may also be present and is believed to be an oxidised equivalent of the beta form. It is further identified in Example 2.

We have found that catalysts produced according to the above process commonly contain a vanadium/phosphorus mixed oxide of the type described as phase X. In a paper by Jordan & Calvo, Canadian Journal of Chemistry 51 2621-5, 1973 the isolation of individual crystals of phase X from a substantially amorphous mass and identification of the X-ray diffraction characteristics of phase X is described.

Catalysts produced in accordance with this invention unlike the product disclosed by Jordan & Calvo possess a high surface area. We have found that in a high surface area catalyst the presence of phase X increases the catalytic effectiveness by conferring on the catalyst attractive activities and selectivities in the oxidation of hydrocarbons to maleic anhydride.

We believe that the proportion of phase X in the catalytically active form is increased by contact of the catalyst precursor to a highly acidic medium at an elevated temperature which is preferable at least 50° C. and more preferably at least 80° C. for example up to 250° and preferably up to 150° C. Thus if for example the vanadium/phosphorus mixed oxide catalyst precursor is precipitated by evaporation of a solution containing a volatile acid, for example one boiling in the above range at atmospheric pressure, for example aqueous HBr or preferably HCl, to dryness as previously described there is a tendency to produce a high phase X content in the catalytic form eventually produced therefrom.

We also believe that a thorough separation of phase E and any other phases coincidentally removed from the catalyst precursor as aforesaid increases the phase X content of the catalytically active form. It is also believed that extracting the precursor in water or the aforesaid solvent by removing unwanted phases increases the surface area of the catalytically active form.

The invention therefore also comprises a catalyst for the oxidation of hydrocarbons to acid anhydrides especially maleic anhydride which comprise at least 5% and preferably at least 15% by weight of phase X, the catalyst having a surface area of at least 7 square meters per gram and preferably at least 10 square meters per gram. More preferably the catalyst comprises considerably more for example at least 40% and more preferably at least 50% by weight of phase X. The phase X content may be estimated from the integrated intensity of its characteristic lines in an X-ray diffraction pattern. If desired an internal standard may be used in such estimations.

It is preferred that the catalyst should contain less than 15% and more preferably less than 10% of amorphous vanadium/phosphorus mixed oxides. It is also preferred that if the catalyst contains vanadium/phosphorus mixed oxides other than as phase X, they should be at least partly present as phase B or B'.

If desired a catalyst promoter may be incorporated in the catalyst. Such a promoter may be tungsten, nickel, cadmium, zinc, bismuth, lithium, copper, uranium, zirconium, hafnium, chromium, iron, manganese, molybdenum and/or preferably cobalt and/or a rare earth promoter for example cerium or more preferably lanthanum, the atomic ratio of the promoter to vanadium being preferably in the range 0.0015:1 to 1:1. The promoter may be incorporated in the catalyst by including a suitable compound in the solution from which the vanadium/phosphorus mixed oxide is precipitated or may be introduced to the precursor immediately after precipitation, after boiling or after activation of the catalyst suitably by physical admixture or preferably by impregnating the solid with a solution of a suitable compound of the promoter and drying the impregnated solid. Vanadium/phosphorus mixed oxide catalysts having surface areas greater than 10, more preferably greater than 15 $m^2$/gram promoted with rare earth metal promoters especially lanthanum and/or cerium are believed to be novel.

The atomic ratio of vanadium to phosphorus is preferably in the range 0.5:1 to 2:1, and is preferably in the range 1:0.8 to 1:1.7.

It is preferred that the surface area of the catalyst should be at least 10 $m^2$/g after the phase transition and it is more preferably at least 15 $m^2$/g for example in the range 10 or 15 to 50 $m^2$/g. Preferably the surface area does not exceed 150 $m^2$/g and more preferably it is <70 $m^2$/g.

The vanadium compound may be introduced to the solution by dissolving for example vanadium pentoxide, vanadium-sesqui-oxide, a vanadyl halide for example $VOCl_2$, a vanadium oxytrihalide, a vanadium-oxydihalide, vanadyl sulphate or vanadium (V) phosphate in the solvent. Preferably an acid stronger than phosphoric acid is present for example hydrochloric, hydrobromic, sulphuric or nitric acid. Such acids may be formed in situ from anions present in the vanadium compound or for example by hydrolysis of phosphorus oxytrihalides. The phosphoric acid may be supplied as ortho-phosphoric acid or its metal salts for example sodium dihydrogen phosphate, as monofluoro phosphoric acid, phosphorus pentoxide, a phosphorus oxytrihalide or as a condensed phosphorus acid for example pyrophosphoric acid or tripolyphosphoric acid. Such acids are converted to phosphoric acid if for example water is present. If desired a reducing agent for example oxalic, formic, citric or other reducing carboxylic acid may be added to reduce vanadium (V) to vanadium (IV).

Suitably the catalyst may be treated with a suspension of an inert support for example an alumina, silicon carbide, Kieselguhr, pumice or preferably silica support. A suitable coloidal silica sol is for example the material supplied under the trademark "LUDOX" by E. I. Du Pont de Nemours & Co. Such supports may be incorporated into the catalyst or into the precursor, or the precursor may be formed from a solution incorporating such supports. The surface area of the catalyst excluding the reinforcement or support may be determined directly when the catalyst is prepared first and the reinforcement or support is added subsequently. If the catalyst is formed on a reinforcement or support however the surface area of the catalyst according to this invention is defined as that which is possessed by a catalyst identically prepared but in the absence of the reinforcement or support.

The solution from which the precursor is obtained is preferably an aqueous solution but may if desired comprise also an organic solvent for example isobutanol or tetrahydrofuran. Preferably at least 1 gram molecule of water per gram atom of vanadium is present. Suitably the solvent is water only.

If desired catalysts may be prepared according to the invention by reacting a compound of vanadium with phosphoric acid preferably in the presence of a suitable solvent, for example water and/or a lower alcohol for example methanol, to produce a form of alpha $VOPO_4$ which is then conditioned in the presence of a strong acid for example hydrochloric acid at elevated temperatures as aforesaid. The conditioned precipitate may then be extracted with water or another solvent for phase E and converted to a catalytically active form by heating until a phase transition occurs as aforesaid.

The invention also comprises a process of oxidising a hydrocarbon as aforesaid to maleic anhydride by contacting it in the presence of oxygen with a catalyst as aforesaid. It is preferred to carry out the process using n-butane as the hydrocarbon and it is suitably fed to the catalyst in a concentration of 0.5–1.5% by volume in air to a fixed or fluidised bed of the catalyst. The oxidation is preferably carried out at a temperature in the range 250°–600° C. and more preferably 300°–450° C. The reaction may be carried out at a pressure of 0.5 to 20 atmospheres absolute and is more preferably carried out at a pressure in the range 1–3 atmospheres.

The invention also comprises a process in which phthalic anhydride is produced by oxidizing orthoxylene or naphthalene with oxygen in the presence of a catalyst according to the invention.

EXAMPLE 1—Comparative Example

Vanadium pentoxide (60.6 g) and concentrated aqueous hydrochloric acid (790 mls) were heated with stirring for about 2 hours to give a dark blue solution. To this solution orthophosphoric acid (88%, 89.1 g) was added and the resulting solution was refluxed for a further period of about 2 hours. The solution was then evaporated to dryness and the resulting solid was dried in an oven at 110° C. The P:V ratio of this catalyst precursor was 1.2:1. A portion of this dried solid was mixed with a pelletting agent sold under the trade name "Sterotex" (2% by wt) and pelletised under a pressure of 17 tons. The pellet was then crushed and sieved to give particles 500–710μ in size and a 5.0 mls portion was charged to a tubular fixed bed reactor. The catalyst was then calcined in situ by heating to 385° C. at a rate of 3° C./min whilst 1.5% n butane by volume in air flowed through the bed at a gas hourly space velocity of 1000 hr$^{-1}$. After 100 hrs the temperature was raised to 450° C. for 1 hour and then lowered to 425° C. After calcination, at a reactor temperature of 425° C., at atmospheric pressure and a GHSV of 500 hrs$^{-1}$ of a mixture of 1.5% by volume n-butane in air the catalyst gave 20% molar pass yield of maleic anhydride at a butane conversion of 34%.

At a reactor temperature of 385° C., atmospheric pressure and GHSV of 500 hr$^{-1}$ the catalyst gave a 9% molar pass yield of maleic anhydride at a butane conversion of 13%. At a reactor temperature of 385° C., atmospheric pressure and GHSV of 1000 hr$^{-1}$ the catalyst gave a 6% molar pass yield of maleic anhydride at a butane conversion of 11%. The surface area of the final catalyst was 3 m$^2$/g.

A sample of the final catalyst was examined by X-ray diffractometry and was found to contain mainly the Beta phase as disclosed in the U.S. Pat. No. 3,985,775. The final catalyst was found to contain less than 5% phase X.

EXAMPLE 2

Vanadium pentoxide (60.6 g) and concentrated aqueous hydrochloric acid (790 mls) were heated with stirring for about 2 hours to give a dark blue solution. To this solution orthophosphoric acid (89.1 g, 88%) was added and the resulting solution was refluxed for a further period of about two hours. The solution was then evaporated to dryness and the resulting solid was dried in an air oven at 110° C. The P:V atomic ratio of this catalyst precursor was 1.2:1. The resulting solid was then boiled with water (20 mls/g. solid) for about 1 hour and filtered hot, washed with a small amount of warm water and dried at 110° C. A portion of the dried solid was mixed with a pelletting agent sold under the trade name "Sterotex" (3% by wt) and pelletised to 17 tons. The pellet was then crushed and sieved to give particles 500–710μ in size and a 5.0 ml portion was charged to a tubular fixed bed reactor. The catalyst was then calcined in situ by the procedure detailed in example 1. After calcination, the catalyst gave a molar pass yield of 48% at a butane conversion of 75% at a reactor temperature of 420° C. and a GHSV of 600 hr$^{-1}$ of 1.5% n-butane by volume in air at atmospheric pressure. At a reactor temperature of 385° C. and GHSV of 600 hr$^{-1}$ the catalyst gave a 33% molar pass yield at a butane conversion of 45%. The surface area of the final catalyst was 9 m$^2$/g. A sample of the final catalyst was examined by X-ray diffractometry and in addition to the X-ray powder diffraction pattern of the beta phase it was found that the characteristic X-ray powder diffraction pattern of phase X and phase B'(which are listed in tables 1 and 2 respectively) were present.

By analysis of the peak areas of the diffracted reflections of the beta phase, phase X and phase B', it was found that 40% phase X was present in the catalyst.

TABLE 1

X-ray powder diffraction of phase X
d(A) spacings were obtained using CuKα radiation.
Only lines from spacings between 4.44 Å and 1.83 Å were measured.

| 2θ | d (Å) | Relative* Intensity |
|---|---|---|
| 20.0 | 4.44 | <1 |
| 21.0 | 4.24 | <1 |
| 24.9 | 3.57 | 6 |
| 29.1 | 3.07 | 5 |
| 29.8 | 3.00 | 10 |
| 39.2 | 2.30 | <1 |
| 40.7 | 2.22 | <1 |
| 42.7 | 2.12 | <1 |
| 46.1 | 1.97 | 1 |
| 47.9 | 1.90 | 1 |
| 49.9 | 1.83 | 1.5 |

*Intensities are normalised to reflection at 2θ = 29.8° being 10.

TABLE 2

X-ray powder diffraction pattern of phase B' (or Y)
d (Å) spacings were obtained using CuKα radiation
Only lines from spacings between 4.58 Å and 2.96 Å were measured.

| d (Å) | Relative* Intensity |
|---|---|
| 4.58 | 3 |
| 4.02 | 10 |
| 3.66 | 2 |
| 3.12 | 6.5 |
| 2.96 | 1 |

*Intensities are normalized to the intensity of d = 4.02 Å being 10.

EXAMPLE 3

Vanadium pentoxide (60.6 g) and concentrated aqueous hydrochloric acid (790 mls) were heated with stirring for about 2 hrs to give a dark blue solution. To this solution orthophosphoric acid (88%, 89.1 g) was added and the resulting solution was refluxed for a further period of about two hours. The solution was then evaporated by distillation to about 200 mls. 200 mls of concentrated aqueous hydrochloric acid were added, the resulting solution was refluxed for a further period of 1 hour and then the solution was evaporated to dryness and the resulting solid was dried in an air oven at 110° C. The P:V ratio of this catalyst precursor was 1.2:1. The resulting solid was then boiled with water (20 mls/g. solid) for about 1 hour and the resulting blue suspension was filtered hot, washed with a small amount of warm water and dried at 150° C. A portion of the dried solid was mixed with a pelletting agent sold under the trade name "Sterotex" (2% by weight) and pelletised under a pressure of 17 tons. The pellet was then crushed and sieved to give particles 500–710μ in size and a 5.0 ml portion was charged to a tubular fixed bed reactor. The catalyst was then calcined in situ by the procedure detailed in Example 1. After calcination, the catalyst gave a molar pass yield of 58.5% at a butane conversion of 94% at a reactor temperature of 405° C. and a GHSV of 642 hr$^{-1}$ of 1.5% n-butane by volume in air at atmospheric pressure. At a reactor temperature of 385° C. and GHSV of 615 hr$^{-1}$ the catalyst gave a 53% molar pass yield at a butane conversion of 79%. At a reactor temperature of 420° C. and a GHSV of 2000 hr$^{-1}$ of 1.5% n-butane in air at atmospheric pressure the catalyst gave 43% molar pass yield of maleic anhydride at a n-butane conversion of 72%. The surface area of the final catalyst was 10 m$^2$/g. A sample of the final catalyst was examined by X-ray diffract ometry and the characteristic X-ray powder diffraction patterns of phase X and phase B' were observed in addition to the X-ray powder diffraction pattern of the beta phase. It was found that 52% phase X present in the final catalyst.

EXAMPLE 4

Part A

A sample of phase E as described by Ladwig (Z. Chem. 1968 vol. 8 pages 307 & 308) was prepared by the following method. Vanadium oxydichloride (29 g) and orthophosphoric acid (100%, 65.5 g) were refluxed in aqueous ethanol for 1 hour. Part of the solvent was then removed by distillation and the blue-green precipitate was collected by filtration and dried at 110° C. for 7 hours. The sample was examined by X-ray diffractometry and was found to exhibit the X-ray spectrum characteristic of phase E as given in Table 3. The sample was then examined by differential thermal analysis (D.T.A.) and was found to exhibit one endothermic transition between 365° C. and 425° C.

Part B

A sample of a vanadium phosphorus catalyst precursor was prepared as described in Example 1 and this was examined by X-ray diffractometry and was found to contain the X-ray spectrum characteristic of phase E as given in Table 1. It was determined by this means that 10% by weight of phase E was present in the catalyst precursor. The catalyst precursor was examined by D.T.A. and was found to exhibit two endothermic transitions, one between 365° C. and 420° C. and one between 425° C. and 485° C. This catalyst precursor gave on pretreatment a final catalyst with a poor performance typical of that exemplified in Example 1.

TABLE 3

| d (Angstrom) | 2Θ(degrees) | Relative* Intensity |
| --- | --- | --- |
| 6.34 | 14.0 | 100 |
| 4.49 | 19.8 | 5 |
| 3.98 | 22.3 | 58 |
| 3.58 | 24.9 | 64 |
| 3.37 | 26.4 | 28 |
| 3.17 | 28.2 | 87 |
| 2.98 | 30.0 | 17 |
| 2.83 | 31.6 | 59 |
| 2.48 | 36.2 | 21 |
| 2.37 | 37.9 | 5 |
| 2.10 | 43.1 | 34 |
| 2.00 | 45.3 | 12 |

TABLE 3-continued

| d (Angstrom) | 2Θ(degrees) | Relative* Intensity |
| --- | --- | --- |
| 1.90 | 47.9 | 6 |
| 1.87 | 48.8 | 6 |
| 1.76 | 52.0 | 8 |
| 1.69 | 54.4 | 5 |
| 1.68 | 54.5 | 7 |
| 1.58 | 58.2 | 12 |
| 1.54 | 60.1 | 8 |

*Relative intensities less than 5 are not quoted

Treatment of the catalyst precursor with boiling water as described in Example 2 resulted in a catalyst precursor which on analysis by X-ray diffractometry showed that the X-ray spectrum of phase E was essentially absent (<1% by wt. phase E present) and on D.T.A. it was found that the endothermic transition at 365° C. to 420° C. was also absent. This catalyst precursor gave on pretreatment a final catalyst with a greatly improved performance typical of that exemplified in Examples 2 and 3.

On evaporation on the extractant water a solid comprising phase E was recovered.

EXAMPLE 5

Part A

A catalyst precursor was prepared as described in Example 1 and was extracted with DMSO (20 mls/1 g solid) at 70° C. for 24 hours. The resulting slurry was filtered hot, washed with a small amount of DMOS and dried at 110° C. in an air oven. A portion of the resulting solid was mixed with "Sterotex" (3% w/w) and pelleted at 17 tons. The pellet was sieved and crushed to give particles 500–710μ in size and a 5 ml portion was charged to a tubular fixed bed reactor. The catalyst was then calcined in situ by heating to 385° C. at a rate of 3° C./min whilst 1.5% n-butane by volume in air flowed through the bed. After 11 hours the temperature was raised stepwise to 450° C. for 2 hours. After calcination at a reactor temperature of 385° C., at atmospheric pressure and a GHSV of 1000 hr$^{-1}$ the catalyst gave a 12% molar pass yield of maleic anhydride at a butane conversion of 15%. A sample of the final catalyst was examined by X-ray powder diffractometry and was found to exhibit the X-ray powder diffraction patterns characteristic of phase X and phase Y in addition to that of the beta phase. The catalyst was found to contain 23% phase X.

Part B

The catalyst precursor prepared as described in Example 1 was examined by X-ray diffractometry and D.T.A. and was found to contain phase E. Treatment of the catalyst precursor with DMSO as described in Example 5 part A resulted in a precursorwhich on analysis by X-ray diffractometry showed that the X-ray diffraction spectrum of phase E was essentially absent. Also on D.T.A. it was found that the endothermic transition at 365°–420° C., characteristic of phase E, was absent.

EXAMPLE 6

A series of final catalysts were prepared by the methods described in Examples 1, 2 and 3. The specific activity of these catalysts was then determined for the oxidation of 1.5% n-butane in air to give maleic anhydride at a reactor temperature of 385° C. and a GHSV of 1000 hr$^{-1}$ at atmospheric pressure. The results are given in Table 4 and these show that the specific activity for the production of maleic anhydride increases with increasing phase X content.

TABLE 4

| Method of Preparation | Surface area m$^2$/g | % phase X in final catalyst | Specific activity moles maleic anhydride produced/m$^2$/hour |
|---|---|---|---|
| Example 1 | 3 | None | 1.3 × 10$^{-5}$ |
| Example 2 | 11 | 37 | 1.43 × 10$^{-5}$ |
| Example 2 | 10 | 42.5 | 2.10 × 10$^{-5}$ |
| Example 3 | 10 | 52.4 | 3.19 × 10$^{-5}$ |

EXAMPLE 7

Vanadium pentoxide (183 g.) and orthophosphoric acid (88%, 414.9 g) were suspended in methanol (2,400 ml). The suspension was refluxed for 5 hours and was then cooled to room temperature and left to stand for 24 hours. The yellow solid prepared was collected by filtration and dried at 115° C. in an air oven. A portion of the solid (81 g) was then slurried with concentrated aqueous hydrochloric acid (100 mls) and was refluxed for 24 hours after which time the slurry had become blue in colour. The slurry was then evaporated to dryness and the solid was dried at 115° C. in an air oven. The resulting solid was then boiled with water (20 mls/g solid) for about 2 hours and the resulting blue suspension was filtered hot and the solid was washed with a little warm water and dried at 150° C. A portion of the dried solid was mixed with a pelleting agent sold under the trade name "Sterotex" (2% by weight) and pelletised under pressure at 17 tons. The pellet was then crushed and sieved to give particles 500–710μ in size and a 5.0 ml portion was charged to a tubular fixed bed reactor. The catalyst was then calcined in situ by the procedure detailed in Example 1. After calcination, the catalyst gave a molar pass yield of 47% at a butane conversion of 87% at a reactor temperature of 420° C. and a GHSV of 1000 hr$^{-1}$ of 1.5% n-butane in air at atmospheric pressure. At a reactor temperature of 385° C. and a GHSV of 1000 hr$^{-1}$ of 1.5% n-butane in air at atmospheric pressure the catalyst gave a molar pass yield of 44% at an n-butane conversion of 68%. The surface area of the final catalyst was 12 m$^2$/g. The final catalyst was examined by X-ray diffractometry and was found to contain in excess of 20% phase X.

EXAMPLE 8

A catalyst precursor was prepared, extracted with water, dried, pelleted and sieved to give 500–710μ particles as described in Example 2. The particles were then heated in a muffle furnace to 400° C. for 12 hours (nitrogen was fed). A sample of the heat treated catalyst was examined by X-ray powder diffractometry and was found to contain the X-ray powder diffraction patterns characteristic of phase X and phase B' with only a small proportion of the beta phase being present. The heat treated catalyst was found to contain about 40% phase X. A 5 ml portion of the heat treated catalyst was loaded to a fixed bed tubular reactor. At a reactor temperature of 420° C. and a GHSV of 1000 hr$^{-1}$ of 1.6% n-butane in air at atmospheric pressure the catalyst gave a 34% molar pass yield of maleic anhydride at a butane conversion of 50%. The surface area of the final catalyst was 7 m$^2$/g.

Examples 9–14 show that the catalytic performance of catalysts containing phase X can be greatly improved by the addition of trace amounts of promoters.

EXAMPLE 9

A catalyst precursor was prepared, extracted with boiling water, dried, pelleted and sieved to give particles 500–710μ in size as described in Example 3. The particles were then dried at 150° C. for 16 hours and were then impregnated with an aqueous solution containing 8 g. per 100 ml of cobalt chloride (as CoCl$_2$ 6H$_2$O) to give a catalyst with a Co:V atomic ratio of 0.04:1. After drying a 5.0 ml portion was charged to a tubular fixed bed reactor and the catalyst was calcined in situ by the procedure detailed in Example 1. After calcination the catalyst gave a molar pass yield of 60% at a butane conversion of 88% at a reactor temperature of 430° C. and a GHSV of 1000 hr$^{-1}$ of 1.5% n-butane by volume in air at atmospheric pressure. The surface area of the final catalyst was 13 m$^2$/g and on analysis by X-ray powder diffraction the final catalyst was found to contain 44% phase X.

EXAMPLE 10

A catalyst was prepared as described in Example 9 except that a solution of cobalt chloride (4–5 g as CoCl$_2$ 6H$_2$O) in isobutanol (25 ml) was used to impregnate the catalyst particles. The Co:V ratio of the catalyst was 0.034:1. After drying a 5.0 ml portion was charged to a tubular fixed bed reactor and the catalyst was calcined in situ by the method detailed in Example 1. After calcination the catalyst gave a molar pass yield of 56% at a butane conversion of 87% at a reactor temperature of 420° C. and a GHSV of 1000 hr$^{-1}$ of 1.5% n-butane in air at atmospheric pressure. The surface area of the final catalyst was 10 m$^2$/g and on analysis by X-ray powder diffraction the catalyst was found to contain 46% phase X.

EXAMPLE 11

A catalyst precursor was prepared, extracted with water, dried, pelleted and sieved to give particles 500–710μ in size as described in Example 3. A series of cobalt promoted catalysts were then prepared using the method given in Example 9 and using aqueous cobalt chloride solutions of different concentration to vary the Co:V atomic ratio. 5 ml portions of the catalyst were then loaded to the reactor and calcined in situ by the method described in Example 1. The catalysts were then used to oxidise 1.5% n-butane in air to maleic anhydride and the results are given in Table 5.

TABLE 5

| V:Co atomic ratio | GHSV hr$^{-1}$ | Reactor Temperature °C. | n Butane conversion % | Maleic Anhydride Molar Pass Yield % | Surface Area m$^2$/g | % Phase X |
|---|---|---|---|---|---|---|
| 0.053:1 | 2000 | 420 | 85 | 58.9 | 15.8 | 35 |
|  | 2500 | 430 | 86 | 57.0 |  |  |
| 0.065:1 | 2000 | 420 | 94.5 | 59.3 | 14 | 40 |
| 0.075:1 | 1600 | 420 | 86.6 | 58.5 | 10 | 41 |

EXAMPLE 12

This example shows the use of lanthanum as a promoter.

A catalyst precursor was prepared, extracted with boiling water, pelleted and sieved to give particles 500–710μ in size as described in Example 3. The particles were then dried at 150° C. in air for 16 hours and were then impregnated with a solution of lanthanum nitrate (2.7 g, La(NO$_3$)$_3$ 6H$_2$O) in isobutanol (25 ml) to give a catalyst with a V:La atomic ratio of 1:0.009. By using a different concentration of lanthanum nitrate in isobutanol (4.6 g/25 ml) a catalyst was prepared with a V:La atomic ratio of 1:0.027. 5 ml portions of these catalysts were then loaded to a fixed bed tubular reactor and calcined as described in Example 1. The catalysts were then used to oxidise 1.5% n-butane in air to maleic anhydride and the results are given in Table 6.

TABLE 6

| V:La atomic ratio | GHSV hr$^{-1}$ | Reactor Temperature °C. | n Butane conversion % | Maleic Anhydride Molar Pass Yield % | Surface Area m$^2$/g | % Phase X |
| --- | --- | --- | --- | --- | --- | --- |
| 1:0.009 | 2000 | 420 | 83 | 60 | 15 | 32 |
| 1:0.027 | 2500 | 420 | 88 | 60 | 18 | 33 |

EXAMPLE 13

A catalyst precursor was prepared, extracted with boiling water, dried, pelleted and sieved to particles 500–710μ in size as described in Example 3. The particles were then dried at 150° C. in air for 16 hours. A series of promoted catalysts were then prepared using a range of promoters by impregnating the catalyst particles with solutions of suitable promoter compounds in isobutanol. 5 ml portions of the promoted catalysts were then loaded to a fixed bed tubular reactor and were then calcined in situ by the method described in Example 1. The promoted catalysts were then used to oxidise 1.5% n-butane in air to maleic anhydride and the results are given in Table 7.

dryness and the resulting solid was dried in an air oven at 110° C. The resulting solid was then boiled with water (20 mls/g solid) for about 2 hours and the resulting suspension was filtered hot, washed with a small amount of warm water and dried at 110° C. The V:Mo atomic ratio of this dried solid was 1:0.043. A portion of the dried solid was mixed with a pelleting agent sold under the trade name "Sterotex" (3% by weight) and was then pelleted under a pressure of 17 tons. The pellet was then crushed and sieved to give particles 500–710μ in size and a 5 ml portion was loaded to a fixed bed tubular reactor. The catalyst was calcined in situ by the method described in Example 1. After calcination, at a reactor temperature of 420° C. and a GHSV of 1000 hr$^{-1}$ of 1.5% n-butane in air at atmospheric pressure the catalyst gave a 55% molar pass yield of maleic anhydride at a n-butane conversion of 75%. The surface area of the final catalyst was 9 m$^2$/g and on analysis by X-ray powder diffraction the final catalyst was found to contain 43% phase X.

EXAMPLE 15

The catalyst used in Example 3 was fed at 370° C. with a gas stream containing 1% o-xylene in air at atmospheric pressure at a GHSV of 1000 hr$^{-1}$. The exit gas was scrubbed with acetone. The conversion of o-xylene was 53% and substantial quantities of phthalic anhydride were produced.

GHSV = gas hourly space velocity measured at room temperature (20° C.) and atmospheric pressure.

All reactions were carried out at atmospheric pressure.

DMSO = dimethyl sulphoxide.

Gas compositions are given as molar %.

TABLE 7

| Promoter | V:Promoter Atomic Ratio | Promoter Compound used for Impregnation | Reactor Temperature °C. | GHSV hr$^{-1}$ | n Butane conversion % | Maleic Anhydride Molar Pass Yield % | Surface Area m$^2$/g | % Phase X |
| --- | --- | --- | --- | --- | --- | --- | --- | --- |
| CHROMIUM | 1:0.004 | Cr(NO$_3$)$_3$9H$_2$O | 385 | 500 | 90 | 57 | 10 | 50 |
|  |  |  | 420 | 1000 | 93 | 50 |  |  |
| COPPER | 1:0.01 | Cu(NO$_3$)$_2$3H$_2$O | 420 | 1000 | 91 | 54 | 12 | 35 |
| CERIUM | 1:0.0125 | Ce(NO$_3$)$_3$6H$_2$O | 440 | 1000 | 95 | 50 | 11 | 50 |
| NICKEL | 1:0.008 | Ni(NO$_3$)$_2$6H$_2$O | 420 | 1000 | 80 | 49 | 12 | 17 |
| ZINC | 1:0.03 | ZnCl$_2$ | 420 | 400 | 90 | 60 | 8.6 | 30 |
|  |  |  | 450 | 1000 | 91 | 59 |  |  |

EXAMPLE 14

This example demonstrates the use of molybdenum as a promoter.

Vanadium pentoxide (60.6 g) and molybdenum trioxide (8 g) and concentrated aqueous hydrochloric acid (760 mls) were heated under reflux with stirring for about 2 hours to give a dark blue solution. To this solution orthophosphoric acid (89.3 g, 88%) was added and the resulting solution was refluxed for a further period of about 2 hours. The solution was then evaporated to The pressure applied in pelletting were applied to an area of 1.1 sq. inches.

We claim:

1. A process of oxidizing butane, a butene or a mixture of butane and a butene to maleic anhydride by contacting it in the vapor phase and in the presence of oxygen with a catalyst which consists essentially of a vanadium/phosphorous mixed oxide having a surface area greater than 10 m$^2$/g and lanthanum as a promoter.

* * * * *